United States Patent
Nanni et al.

(10) Patent No.: US 7,505,558 B2
(45) Date of Patent: Mar. 17, 2009

(54) APPARATUS FOR ACQUIRING AND VISUALIZING DENTAL RADIOGRAPHIC IMAGES AND OPERATING METHOD THEREOF

(75) Inventors: Eros Nanni, Castel Guelfo Di Bologna (IT); Tommaso Virnicchi, Recanati (IT); Pascal Bertossa, Thônex (CH)

(73) Assignee: ELCA Technologies S.r.l., Imola (IT)

( * ) Notice: Subject to any disclaimer, the term of this patent is extended or adjusted under 35 U.S.C. 154(b) by 190 days.

(21) Appl. No.: 11/218,308

(22) Filed: Aug. 31, 2005

(65) Prior Publication Data
US 2006/0083348 A1    Apr. 20, 2006

(30) Foreign Application Priority Data
Oct. 15, 2004    (IT)   ............ BO2004A0638

(51) Int. Cl.
     *G01N 23/04*    (2006.01)
     *H01L 24/146*    (2006.01)
(52) U.S. Cl. .................... 378/62; 250/370.09
(58) Field of Classification Search ............. 378/38, 378/62, 98.8, 115, 116, 168, 189, 191, 204; 250/370.9, 370.09
See application file for complete search history.

(56) References Cited

U.S. PATENT DOCUMENTS

| | | | | |
|---|---|---|---|---|
| 5,938,738 A * | 8/1999 | Mu-Teng | .................. | 719/321 |
| 6,404,854 B1 | 6/2002 | Carroll et al. | | |
| 6,953,935 B1 * | 10/2005 | Hoffman | ................ | 250/370.13 |
| 2001/0055368 A1 * | 12/2001 | Carroll | ..................... | 378/189 |
| 2004/0005032 A1 * | 1/2004 | Nanni et al. | .................. | 378/168 |
| 2004/0066898 A1 | 4/2004 | Schick et al. | | |
| 2004/0198386 A1 * | 10/2004 | Dupray | ..................... | 455/456.1 |
| 2004/0203694 A1 * | 10/2004 | Wong et al. | .................. | 455/419 |
| 2005/0032516 A1 * | 2/2005 | Marchevsky | ............. | 455/426.2 |
| 2005/0211908 A1 * | 9/2005 | Dieras et al. | ........... | 250/370.09 |
| 2005/0255878 A1 * | 11/2005 | Leinonen et al. | ......... | 455/552.1 |
| 2006/0067474 A1 * | 3/2006 | Schmitt | ..................... | 378/102 |
| 2006/0095539 A1 * | 5/2006 | Renkis et al. | ............... | 709/217 |

(Continued)

FOREIGN PATENT DOCUMENTS

DE      89 09 398 U1      10/1989

(Continued)

OTHER PUBLICATIONS

Sairam, et al., Bluetooth in Wireless Communication, Jun. 2002, IEEE Communications Magazine, pp. 90-96.*

(Continued)

*Primary Examiner*—Edward J Glick
*Assistant Examiner*—Anastasia Midkiff
(74) *Attorney, Agent, or Firm*—Graybeal Jackson LLP (57) ABSTRACT

Apparatus for the acquisition and visualization of dental radiographic images comprising an X ray emitter device; a radiographic sensor for the acquisition of a dental radiographic image; a processing unit for storing and visualizing the image; and a communication device adapted to transmit the image acquired by the radiographic sensor to the processing unit according to a predetermined radio communication protocol; the communication device comprising a control module, which is adapted to automatically discriminate the radio communication between the sensor and the processing unit from any communication put into effect by the processing unit from and to devices and apparatuses other than the sensor and utilizing the same predetermined communication protocol implemented by the communication device.

16 Claims, 4 Drawing Sheets

U.S. PATENT DOCUMENTS

| | | | |
|---|---|---|---|
| 2006/0268728 A1* | 11/2006 | Mower et al. | 370/252 |
| 2007/0202890 A1* | 8/2007 | Feher | 455/456.1 |
| 2008/0029707 A1* | 2/2008 | Kari et al. | 250/370.09 |
| 2008/0057886 A1* | 3/2008 | Feher | 455/151.1 |
| 2008/0062856 A1* | 3/2008 | Feher | 370/206 |
| 2008/0159483 A1* | 7/2008 | Connelly et al. | 378/98.2 |

FOREIGN PATENT DOCUMENTS

| | | |
|---|---|---|
| EP | 0 757 474 A | 2/1997 |
| EP | 1 378 201 A | 1/2004 |
| WO | WO 00/29872 A | 5/2000 |

OTHER PUBLICATIONS

Schick Technologies, Inc., "CDR Wireless / SDX Software User Guide", Oct. 11, 2004, Schick Technologies, Inc., USA, XP002360238.

European Search Report for EP 05 10 5371 mailed Jan. 16, 2006.

* cited by examiner

APPARATUS FOR ACQUIRING AND VISUALIZING DENTAL RADIOGRAPHIC IMAGES AND OPERATING METHOD THEREOF

PRIORITY CLAIM

This application claims priority from Italian patent application No. BO2004A 000638, filed Oct. 15, 2004, which is incorporated herein by reference.

TECHNICAL FIELD

The present invention relates to an apparatus for acquiring and visualizing dental radiographic images, and to the operating method thereof.

BACKGROUND

As it is known, in dentistry there are often used apparatuses which are capable of acquiring a patient's dental radiographic image for then showing the image itself on a visualization monitor.

In particular, the aforementioned apparatuses are typically provided with an emitter device adapted to generate a beam of X rays towards the patient's oral cavity; with a radiographic sensor adapted to acquire a radiographic image of the oral cavity generating by the emitter device; and with a computer which is adapted to store and visualize on a respective monitor the radiographic image acquired by the sensor.

The last generation apparatuses are equipped, moreover, with a communication device of the wireless type, which is capable of receiving and transmitting radio signals between the computer and the radiographic sensor so to permit the computer to transmit to the radiographic sensor the commands for acquiring the radiographic images and to the radiographic sensor itself to transmit to the computer the radio signals containing the data related to the acquired radiographic image. In particular, the communication device receives and transmits data by implementing a standard communications protocol.

A problem connected to the aforementioned apparatuses is the need by the dentist to configure, in the initial step of use of the apparatus itself, a communication channel between the computer and the radiographic sensor/s in the range of action of the communication device so to ensure a correct reception and transmission of the commands and the radiographic images between each radiographic sensor and the computer via the established communication channel.

Indeed, it often occurs that at the apparatus and therefore the communication device, there are present in addition to the radiographic sensors also other types of apparatuses or devices using the same standard communication protocol implemented by the communication device.

Such apparatuses or devices typically consists of cellular telephones, headphones or players, which, during the initial identification step of the radiographic sensors implemented by the computer are indistinctively acknowledged by the computer itself. So the dentist, after acknowledging the various communicating devices and apparatuses made by the computer is forced to select the acknowledged radiographic sensor or sensors distinguishing them from the other identified apparatuses and devices, thus configuring the communication channel or channels between the computer and the sensors.

This operation, in addition to creating an inconvenience for the dentist in terms of time and therefore of costs, may determine an incorrect operation of the apparatus if the configuration of the communication channels between the computer and the radiographic sensors is performed incorrectly by the dentist him or herself.

It is also known that in some radiographic image acquisition and visualization apparatuses of the type mentioned above, the radiographic sensor, after a predetermined stand-by time after its activation, is automatically deactivated to impede an accumulation of electrons in its cells.

If on one hand such automatic deactivation of the radiographic sensor prevents the deterioration of the image caused by excessive accumulation of electrons in the cells, on the other it considerably increases the risk of exposing the patient to an unnecessary dose of X rays, if the emission device is activated by the dentist in an instant after the predetermined stand-by time of the sensor.

SUMMARY

It is the object of the present invention to obtain an apparatus for the acquisition and visualization of dental radiographic images, which is capable of discriminating entirely automatically the radio communication actuated by the radiographic sensor/s belonging to the apparatus from the possible communications made by the latter with apparatuses or devices other than the radiographic sensors themselves, and is adapted to synchronize the image acquisition sensor with the X ray beam emission instantly.

According to the present invention, it is provided an operating method of an apparatus for acquiring and visualizing dental radiographic images as recited in the attached claims.

According to the present invention, it is also obtained an apparatus for the acquisition and visualization of dental radiographic images as recited in the attached claims.

BRIEF DESCRIPTION OF THE DRAWINGS

The present invention will now be described with reference to the attached drawings, which illustrate a non-limitative example of embodiment, in which:

FIG. 4 shows a first part of a flow chart indicating the operations implemented by the apparatus during its operation; while

DETAILED DESCRIPTION

Figure 1:
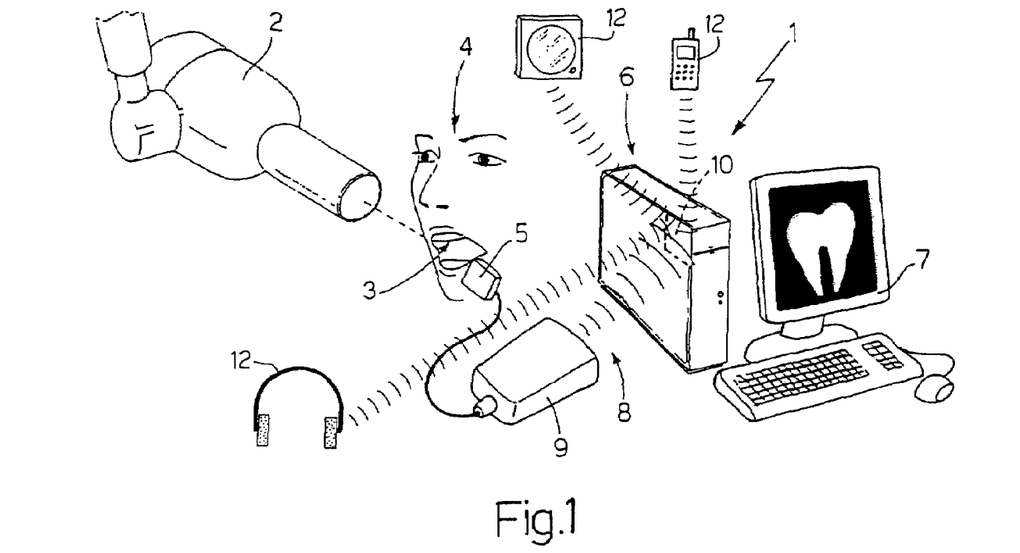
FIG. 1 is an exploded perspective view of a preferred embodiment of the apparatus according to the present invention.

With reference to FIG. 1, numeral 1 indicates, as a whole, an apparatus for the acquisition and visualization of radiographic dental images comprising at least one emitter device 2 adapted to address a beam of X rays to the oral cavity 3 of a patient 4; at least one radiographic sensor 5 adapted to acquire a radiographic image of the oral cavity 3 generated by the device 2; and a processing unit 6 adapted to store and visualize on a respective monitor 7 the radiographic image acquired by the radiographic sensor 5.

The emitter device 2 is of the known type and therefore will not be described further, while the processing unit 6 may consists of an electronic computer equipped with the dental radiographic image visualization monitor 7.

Figure 2:
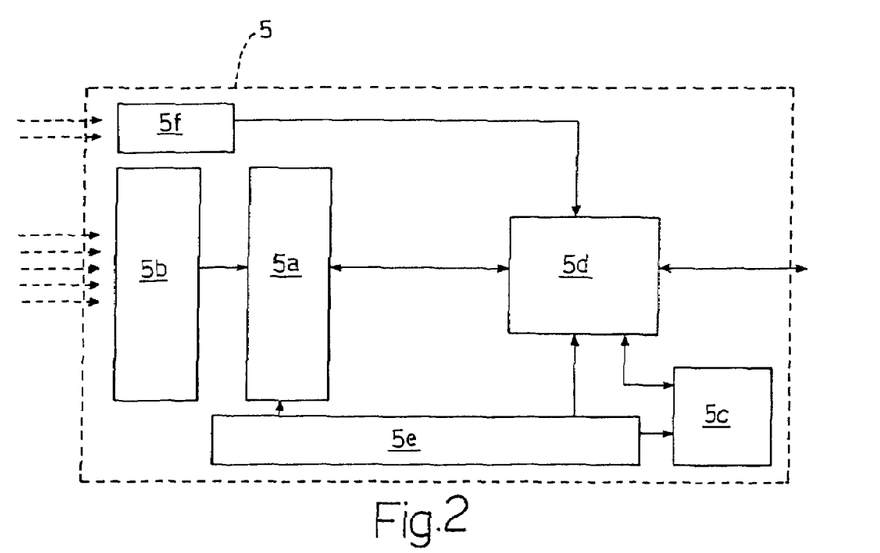
FIG. 2 shows an electrical block diagram of a radiographic sensor of the apparatus shown in FIG. 1.

With reference to FIG. 2, the radiographic sensor 5 essentially comprises a CCD sensor 5a or, alternatively, a CMOS sensor, and scintillator device 5b coupled with the CCD sensor 5a or CMOS itself; a storage device 5c, for example a RAM, adapted to store the acquired radiographic image; a processing device 5d capable of piloting the CCD sensor 5a during the radiographic image acquisition and adapted to store the acquired radiographic image in the storage device 5c; and a feeding device 5e comprising a battery, which is adapted to feed a predetermined voltage/current to the various devices comprised in the radiographic sensor 5.

The radiographic sensor 5 comprises, moreover, a photodiode 5f, which is arranged at the CCD sensor 5a and is adapted to output an electrical signal of amplitude correlated to the intensity of the X ray beam emitted towards the patient's oral cavity 4, that is towards the CCD sensor 5a itself.

With reference to FIG. 1, the apparatus 1 comprises, moreover, a communication device 8, which is adapted to receive and transmit the radiofrequency data between the processing unit 6 and the radiographic sensor 5 according to a determined radio communication protocol.

In particular, the communication device 8 comprises two communication interfaces, which work preferably according to the BLUETOOTH radio communication protocol to actuate the communication between the radiographic sensor 5 and the processing unit 6.

The first communication interface, indicated hereinafter by numeral 9, is connected to the radiographic sensor 5 to provide to the latter the commands received from the processing unit 6 and/or to transmit to the same the radiographic images acquired by the radiographic sensor 5, while the second communication interface, indicated hereinafter by numeral 10, is connected to the processing unit 6 for transmitting the commands to be given to the radiographic sensor 5 and/or to receive the radiographic images acquired and transmitted by the radiographic sensor 5 itself.

Unlike the apparatuses of the known type, the communication interface 10 is capable of discriminating fully automatically the radiofrequency communication made by the radiographic sensor 5 according to the BLUETOOTH protocol from other radiofrequency communications implemented with a same communication protocol by a series of devices or apparatuses 12 present at the processing unit 6 within the range of action of the communication interface 10, so to selectively address the subsequent communications made by the communication interface 10 via a preferential communication channel from and to the communication interface 9 connected to the radiographic sensor 5.

Figure 3:
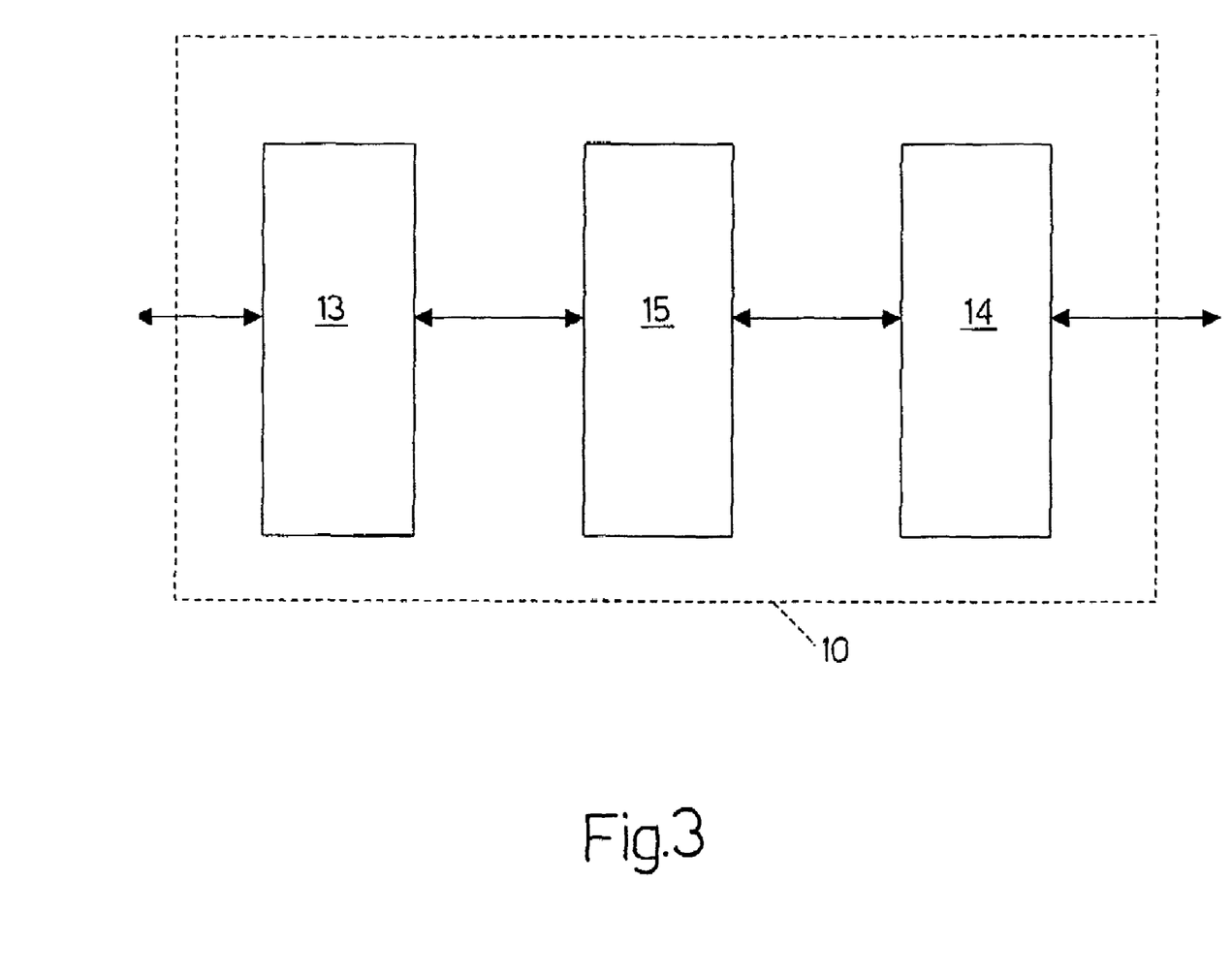
FIG. 3 schematically shows a communication interface of the apparatus shown in FIG. 1.

With reference to FIG. 3, the communication interface 10 comprises essentially a receiving and transmitting module 13, which is adapted to receive and transmit in radiofrequency the data from and to the communication interface 9 according to the BLUETOOTH communication protocol, and an image management module 14, which is adapted to receive from the receiving and transmitting module 13 the dental radiographic image acquired by the radiographic sensor 5 to send it to a processing module (not shown) comprised in the processing unit 6, which in turn controls the visualization of the image via the monitor 7.

In particular, the image management module 14 is adapted to implement a standard image management protocol to permit the acquisition and the management of the images themselves to any type of commercial software implemented in the processing module (not shown) of the processing unit 6 and adapted to manage the visualization of the image on the monitor 7. In the case in point, the image management protocol implemented by the image management module 14 may be, for example, the TWAIN protocol or the STI (abbreviation of "Still Image application programming interface") protocol.

The communication interface 10 comprises, moreover, a control module 15, which is arranged between the receiving and transmitting module 13 and the image management module 14, and is capable of performing a series of operations, described in detail below, to discriminate the radiographic sensor 5 from the other devices or apparatuses 12 present in the range of action of the apparatus 1, so to configure a preferential communication channel between the radiographic sensor 5 and the processing unit 6.

Figure 4:
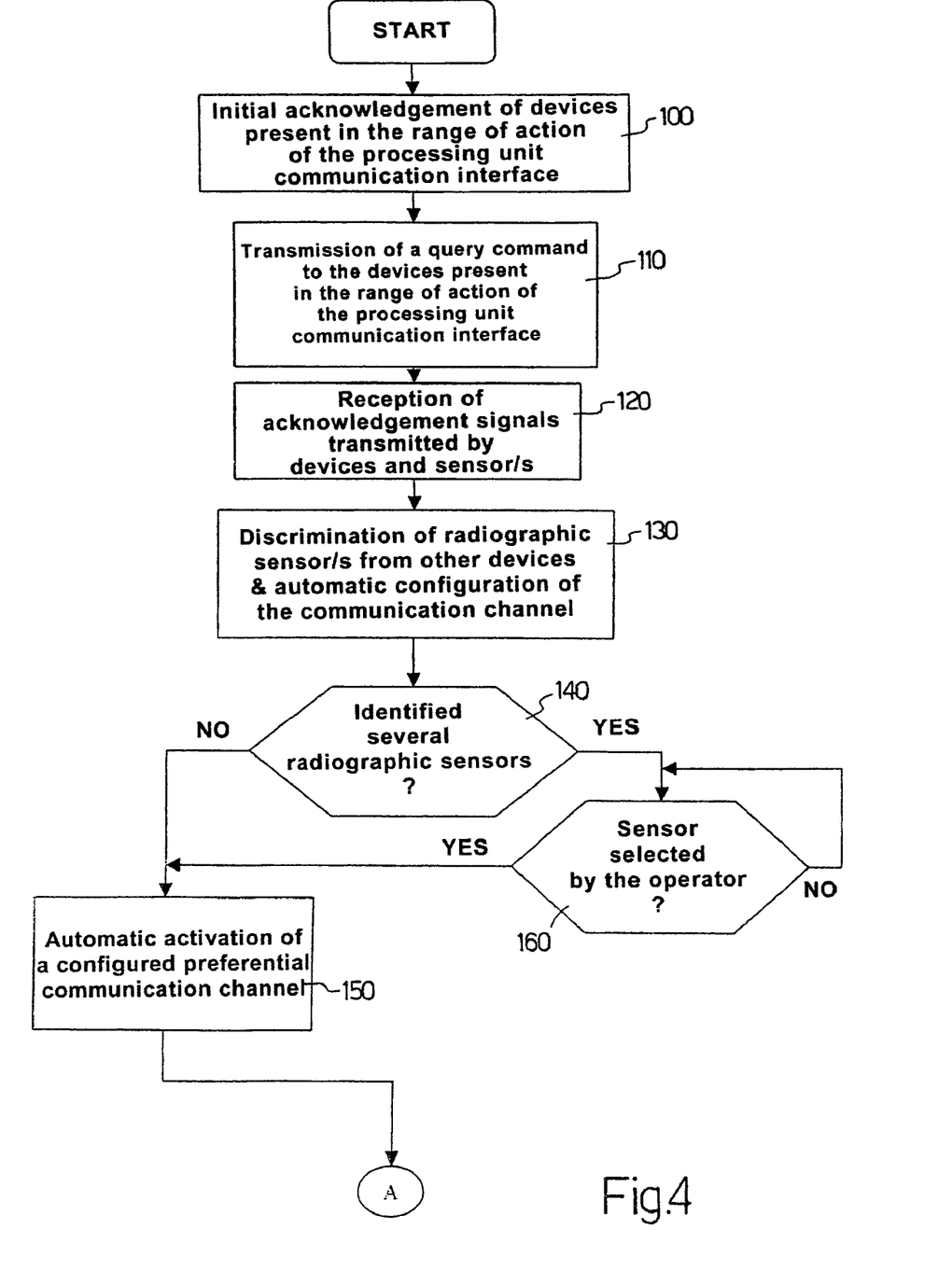
Figure 5:
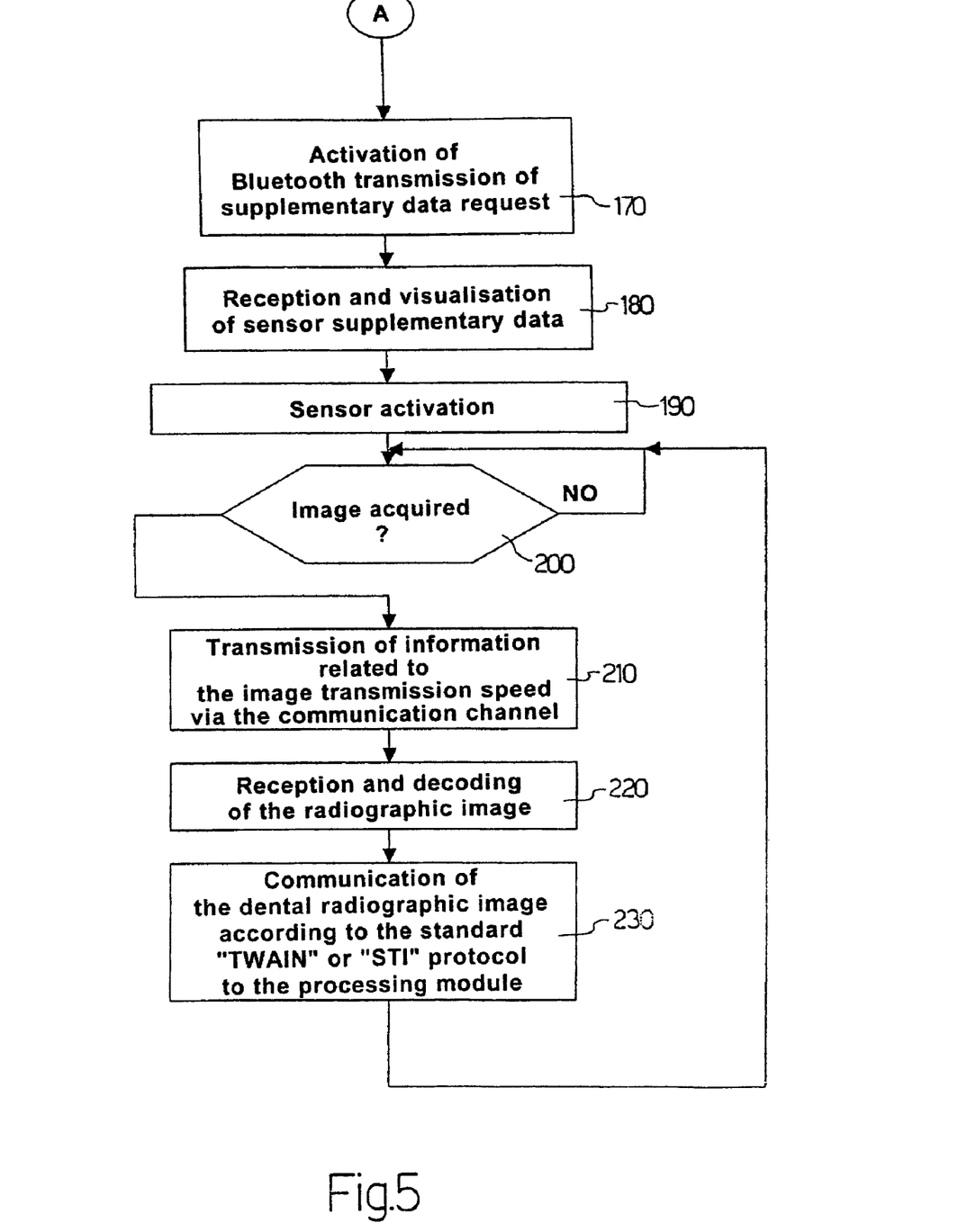
FIG. 5 shows the second part of the flow chart shown in FIG. 4.

FIGS. 4 and 5 show a flow chart indicating the operations implemented by the apparatus 1 during its operation, in which is it assumed that the apparatus 1 has not received or transmitted any data, that is has not yet identified the radiographic sensor 5. In other words, it is assumed that the apparatus 1 has not performed any configuration of the communication channel between the processing unit 6 and the radiographic sensor 5.

It must be said that the apparatus 1 may comprise several radiographic sensors 5, and that therefore, in the operation described below, it will be considered also a condition of discrimination of a series of radiographic sensors 5 from the other devices or apparatuses 12 present in the range of action of the communication interface 10.

Initially, the image management module 14 communicates a control signal, via the control module 15 to the receiving and transmitting module 13, to activate an initial acknowledgement operation of the radiographic sensors 5 and of the devices or apparatuses 12 present in the range of action of the communication interface 10, which are capable of establishing a wireless communication with the same communication protocol implemented by the communication interfaces 9 and 10, that is the BLUETOOTH protocol (block 100).

Once activated, the receiving and transmitting module 13 transmits a query command to the radiographic sensors 5 and the devices or apparatuses 12 present in the range of action of the communication interface 10 (block 110). In this step, following the reception of the query command, each device or apparatus 12 and/or each radiographic sensor 5 transmits to the receiving and transmitting module 13 an acknowledgement signal containing a series of indications which characterize the type of device or apparatus 12 or the radiographic sensor 5. At this point, the receiving and transmitting module 13 receives the acknowledgement signals transmitted by the devices or apparatuses 12 and by the sensor/s 5 (block 120), and the control module 12 proceeds to discriminate the acknowledgment signals which identify the sensor/s 5 from the acknowledgement signals which identify the remaining devices or apparatuses 12 (block 130).

During this step, the control module 15 provides to the image management module 14 the data associated solely to the identified sensor/s 5 and automatically activates the configuration of the preferential communication channel/s for a communication between the identified sensor/s 5 and the processing unit 6, thus excluding any possibility of radio communication between the latter and the acknowledged devices or apparatuses 12 other than sensor 5. The image management module 14 thus sends the data related to the acknowledged sensor/s 5 and to the respective preferential communication channels established by the management and visualization program implemented by the processing module (not shown) which visualizes such information on the monitor 7.

At this point, the image management module 14 checks whether the number of identified sensors 5 is higher than one (block 140). In negative case (NO output from block 140), that is if there is only one radiographic sensor 5, the image management module 14 automatically controls, via the control module 15 the activation of the previously configured preferential communication channel for actuating the communications between the receiving and transmitting module 13 and the radiographic sensor 5 itself (block 150). If instead the number of identified sensors 5 is higher than one (YES output from block 140), the image management module 14 waits for a selection condition of one of the sensors 5 by the operator (block 160). It must be said that if the control module 15 has detected several sensors 5, the management and visualization program will provide on the monitor 7 the indications referred to each radiographic sensor 5 whereby allowing the operator to select them singularly to activate the automatic configuration of the preferential communication channel associated to the selected radiographic sensor 5. Obviously, according to a different embodiment, if several sensors 5 are detected, the control module 15 may be capable of assigning to each acknowledged radiographic sensor 5 a corresponding preferential communication channel according to a predetermined automatic allocation sequential procedure. Alternatively, the module 15 could select one of the available sensors 5 according to any programmable criterion, for example by selecting the last sensor 5 used during the previous acquisition.

After receiving, either automatically or manually, the selection command of a radiographic sensor 5, the image management module 14 controls, via the control module 15, the activation of the preferential communication channel associated to the selected radiographic sensor 5 (block 150). In particular, the preferential communication channel activated by the control module 15 is used for any subsequent data communication between the processing unit 6 and the selected radiographic sensor 5.

With reference to FIG. 5, following the configuration of the preferential communication channel, the image management module 14 controls preferably, but not necessary, the receiving and transmitting module 13, via the control module 15, the transmission of a request for supplementary information to the radiographic sensor 5 (block 170). The radiographic sensor 5 once received the request transmits via the preferential communication channel to the receiving and transmitting module 13 the information concerning the energy state of the battery 5e, and a series of other information on the state of operation of the radiographic sensor 5 itself.

The receiving and transmitting module 13 following the reception of the supplementary information sends them via the control module 15 to the image management module 14 that provides to send them to the processing module (not shown) of the processing unit 6 for visualizing them on the monitor 7 (block 180).

At this point, the image management module 14 sends to the control module 15 an activation command of the radiographic sensor 5 upon acquisition of the radiographic image. The control module 15 transmits via the receiving and transmitting module 13 the activation command to the radiographic sensor 5 (block 190) and waits to acquire the image from the radiographic sensor 5 itself (block 200).

The foresaid waiting condition ends (YES output from block 200) when the radiographic sensor 5 has completed acquisition of the dental radiographic image. It must be said that during this step, the processing device 5d is capable of temporarily storing the dental radiographic image acquired in the storage device 5c so to be able to transmit it, when acquisition is complete or at a later instant, via the preferential communication channel to the receiving and transmitting module 13 using a compression and/or transmission modality directly selectable by the operator.

During this step, the image management module 14 transmits to the radiographic sensor 5, via the receiving and transmitting module 13, a series of indications concerning the transmission speed of the data encoding the acquired radiographic image (block 210) requested by the image management and visualization program implemented by the processing module (not shown). For example, the image management and visualization program implemented by the processing module 14 may envisage, in addition to traditional functions for visualizing high resolution images which require a relatively low transmission speed, also a function for previewing the image ("Preview" function) requiring a faster data transmission speed, because the image must be visualized relatively quickly and with a relatively low definition.

At this point, the processing device 5d of the radiographic sensor 5 controls the communication interface 9 to transmit the image stored in the storage device 5c via the preferential communication channel at a data transmission speed indicated by the image management module 14.

The receiving and transmitting module 13 receives the dental radiographic image (block 220) and communicates it to the control module 15 which decodes and decompresses the data to provide the radiographic image in a given standard graphic format to the image management module 14.

At this point, the image management module 14 makes available the dental radiographic image according to the "TWAIN" or "STI" standard protocol to the processing module (not shown) which in turn visualizes it on the monitor 7a by the image management and visualization program (block 230).

After actuating the visualization of the dental radiographic image on the monitor 7, the interface 10 places itself in stand-by condition waiting for a new acquisition of a dental radiographic image by the radiographic sensor 5 (block 200).

During the stand-by condition of new image acquisition, that is in absence of the X ray beam, the processing device 5d activates cyclically, via a clock signal, the CCD sensor 5a so to impede saturation of the respective cells caused by the accumulation of thermal electrons on them.

The cyclical activation condition of the CCD sensor 5a ends when the photodiode 5f, detecting the presence of a new beam of X rays, sends a signal to the processing device 5d indicating a value correlated to the intensity of the detected X rays. At this point, the processing device 5d may be capable of controlling whether the intensity of the detected X rays fulfils a given relation with a predetermined threshold and when the relation occurs controls the interdiction of the CCD sensor 5a cyclical activation (integration time) to then later activate the acquisition of the dental radiographic image from the CCD sensor 5a via the processing device 5d.

From the foregoing description, it must be said that thanks to the photodiode 5f it is possible to synchronize the instant of activation of the radiographic sensor 5 with the instant of emission of the X rays determining in such a way a considerable reduction of the risk of unnecessary emission of X rays towards the patient with obvious benefits for the latter. Indeed, in this case, a delay in the activation of the emitter device 2 by the dentist will not compromise the correct acquisition of the dental image.

The apparatus 1 presents, moreover, the big advantage of identifying the sensors 5 discriminating them from the other devices or apparatuses 12 present in the range of action of the communication interface 10, and of configuring fully automatically the preferential communication channel between each detected sensor 5 and the processing unit 6. In this way, it is cancelled the need by the dentist or an operator to manually configure the communication channels dedicated to the reception and transmission of the data between radiographic sensors 5 and the processing unit 6 determining an evident saving of time and thus of costs for the dentist, and contextually ensuring the correctness of the configuration of the communication channels used.

Finally, it appears clear that changes and variations may be implemented to the apparatus 1 here described and illustrated without departing from the scope of the present invention.

What is claimed is:

1. An operating method of an apparatus for the acquisition and visualization of dental radiographic images comprising at least one X ray emitter device; at least one radiographic sensor for the acquisition of a dental radiographic image; a processing unit for storing and visualizing said image; and communication means adapted to transmit the image acquired by the radiographic sensor to the processing unit according to a predetermined radio communication protocol; said method comprising:

discriminating automatically a radio communication put into effect between said at least one radiographic sensor and said processing unit from any other radio communication put into effect by said processing unit from and to other devices or apparatuses different from said at least one radiographic sensor, and adapted to communicate according to said predetermined radio communication protocol used by said communication means, wherein said discriminating occurs prior to establishing a preferential communication channel between said at least one radiographic sensor and said processing unit;

identifying, on the basis of said discrimination, said at least one radiographic sensor prior to establishing said preferential communication channel between said at least one radiographic sensor and said processing unit; and automatically configuring said preferential communication channel between said at least one radiographic sensor and said processing unit on the basis of said identification.

2. A method according to claim 1, characterized in that said communication discrimination step of said radiographic sensor is preceded by the steps of: transmitting a query command to said at least one radiographic sensor and to said devices or apparatuses present in a range of action predetermined by said processing unit, receiving a series of identification signals each containing a series of information related to said radiographic sensor and/or said devices or apparatuses; said discrimination step comprises the step of discriminating the information associated to said radiographic sensor identified by the information associated to said devices or apparatuses.

3. A method according to claim 1, characterized in that said predetermined communication protocol is the Bluetooth communication protocol.

4. A method according to claim 1, characterized in that it comprises the step of receiving via said preferential communication channel a plurality of data encoding the dental radiographic data acquired by said at least one radiographic sensor; decoding said data for providing said image according to a standard graphic format; and providing said image according to a predetermined image management protocol to an image management and visualization program.

5. A method according to claim 4, characterized in that said predetermined image management protocol is the "TWAIN" protocol or the "STI" protocol.

6. A method according to claim 1, characterized in that it comprises the step of temporarily storing said acquired image in a storage means of said radiographic sensor.

7. A method according to claim 1, characterized in that it comprises the steps of communicating to said at least one radiographic sensor, a predetermined transmission speed of the data encoding the acquired image, and of transmitting said image from said radiographic sensor to said processing unit via said preferential communication channel at a transmission speed equal to said predetermined transmission speed.

8. A method according to claim 1 in which said radiographic sensor comprises at least one photodiode adapted to output a signal representing a value correlated to the intensity of the detected X rays; said method being characterized in that it comprises the steps of verifying whether said X ray value detected by said photodiode fulfils a given relation with a predetermined threshold; and, when said relation occurs, of activating the radiographic sensor for acquiring said image.

9. An apparatus for the acquisition and visualization of dental radiographic images comprising at least one X ray emitter device; at least one radiographic sensor for the acquisition of a dental radiographic image; a processing unit for storing and visualizing said image; and communication means adapted to transmit the image acquired by the radiographic sensor to the processing unit according to a predetermined radio communication protocol; said apparatus being characterized in that said communication means comprise control means which are adapted to automatically discriminate the radio communication put into effect between said at least one radiographic sensor and said processing unit from any radio communication put into effect by said processing unit from and to devices or apparatuses other than said radiographic sensor prior to establishing a preferential communication channel between said at least one radiographic sensor and said processing unit and using said predetermined communication protocol implemented by the communication means, for identifying said at least one radiographic sensor prior to establishing said preferential communication channel between said at least one radiographic sensor and said processing unit, and means adapted to automatically configure said preferential communication channel between said at least one identified radiographic sensor and said processing unit responsive to said communication means identifying said at least one radiographic sensor.

10. An apparatus according to claim 9, characterized in that said communication means comprise at least one first communication interface connected to said radiographic sensor, and a second communication interface connected to said processing unit; said second communication interface comprising a receiving and transmitting module adapted to communicate according to said predetermined communication protocol with said first interface for receiving the acquired image; an image management module adapted to send said sensor an image according to a predetermined image management protocol to an image visualization module of said processing unit; and said control means, whose function is to decode the image received from said receiving and transmitting module to communicate it in a predetermined graphic format to said image management module.

11. An apparatus according to claim 9, characterized in that said radiographic sensor comprises memory means, and processing means adapted to temporarily stored said dental radiographic image in said memory means.

12. An apparatus according to claim 9, characterized in that said radiographic sensor comprises at least one photodiode adapted to provide to said processing means a signal containing a value correlated to the intensity of the X rays emitted by said emitter device.

13. An apparatus according to claim 9, characterized in that said predetermined communication protocol is the Bluetooth communication protocol.

14. An apparatus according to claim 9, characterized in that said image management protocol is the "TWAIN" protocol or the "STI" protocol.

15. A method, comprising:

sending a query from a processing unit to a plurality of radio-frequency devices that each uses a common communication protocol and includes at least one dental radiographic sensor, wherein the query occurs prior to establishing a communication channel between the at least one radiographic sensor and the processing unit;

receiving information from the plurality of radio-frequency devices indicating a functionality of each radio-frequency device, wherein the receiving occurs prior to establishing a communication channel between the at least one radiographic sensor and the processing unit; and automatically configuring a communication channel between the processing unit and only the at least one radiographic sensor responsive to the received information.

16. The method of claim 15 wherein sending a query to a plurality of radio-frequency devices that each uses a common communication protocol comprises sending the query to the plurality of radio-frequency devices that each uses Bluetooth communication protocol.

* * * * *

UNITED STATES PATENT AND TRADEMARK OFFICE
CERTIFICATE OF CORRECTION

PATENT NO. : 7,505,558 B2  Page 1 of 1
APPLICATION NO. : 11/218308
DATED : March 17, 2009
INVENTOR(S) : Nanni et al.

It is certified that error appears in the above-identified patent and that said Letters Patent is hereby corrected as shown below:

Column 8 line 56 claim 10: delete "said" after "send"
Column 8 line 57 claim 10: delete "sensor" before "an image"

Signed and Sealed this

Twenty-first Day of April, 2009

JOHN DOLL
*Acting Director of the United States Patent and Trademark Office*